(12) United States Patent
Clarke

(10) Patent No.: US 6,360,679 B1
(45) Date of Patent: Mar. 26, 2002

(54) SANITARY WASTE DISPOSAL UNIT

(75) Inventor: Howard Morgan Clarke, Liss (GB)

(73) Assignee: Morgan Automation Limited, Hampshire (GB)

( * ) Notice: Subject to any disclaimer, the term of this patent is extended or adjusted under 35 U.S.C. 154(b) by 0 days.

(21) Appl. No.: 09/807,089

(22) PCT Filed: Oct. 7, 1999

(86) PCT No.: PCT/GB99/03332

§ 371 Date: Apr. 9, 2001

§ 102(e) Date: Apr. 9, 2001

(87) PCT Pub. No.: WO00/20801

PCT Pub. Date: Apr. 13, 2000

(30) Foreign Application Priority Data

Aug. 10, 1998 (GB) ............................................... 9821850

(51) Int. Cl.[7] ............................... F23G 5/02; F23G 5/10
(52) U.S. Cl. ....................... 110/342; 110/346; 110/219; 110/229; 110/238; 110/250
(58) Field of Search ................................ 110/218, 219, 110/229, 230, 231, 238, 241, 250, 301, 302, 342, 346, 101 R; 373/60, 81

(56) References Cited

U.S. PATENT DOCUMENTS

| | | | | |
|---|---|---|---|---|
| 4,050,900 A | * | 9/1977 | Hobbs et al. ............. 23/277 R |
| 4,084,521 A | * | 4/1978 | Herbold et al. ............. 110/242 |
| 4,213,404 A | * | 7/1980 | Spaulding .................. 110/229 |
| 4,402,738 A | * | 9/1983 | Akio ........................... 75/44 S |
| 4,452,154 A | * | 6/1984 | Kono et al. ................. 110/346 |
| 4,759,300 A | * | 7/1988 | Hansen et al. .............. 110/229 |
| 4,934,283 A | * | 6/1990 | Kydd .......................... 110/246 |
| 5,101,739 A | * | 4/1992 | Nance et al. ............... 110/229 |
| 5,323,716 A | * | 6/1994 | Eshelman ................... 110/255 |
| 5,333,146 A | * | 7/1994 | Vance .......................... 373/60 |
| 5,411,714 A | * | 5/1995 | Wu et al. .................... 422/232 |
| 5,417,170 A | * | 5/1995 | Eshelman ................... 110/235 |
| 5,541,386 A | * | 7/1996 | Alvi et al. ............. 219/121.38 |
| 6,199,492 B1 | * | 3/2001 | Kunstler ..................... 110/342 |

FOREIGN PATENT DOCUMENTS

| | | |
|---|---|---|
| GB | 2310485 | 8/1997 |
| WO | 9817950 | 4/1998 |

* cited by examiner

*Primary Examiner*—Denise L. Esquivel
*Assistant Examiner*—K. B. Rinehart
(74) *Attorney, Agent, or Firm*—Ware, Fressola, Van Der Sluys & Adolphson LLP

(57) ABSTRACT

A sanitary waste disposal unit (1) including a scalable destruction chamber (11), a vacuum pump (23), a source of heat (15) and means (29) for the controlled introduction of air into the chamber (11). In use the waste is introduced on the chamber (11) which is then evacuated to remove substantially all the oxygen, and heated to sterilize the waste material to approximately 300–500° C. The chamber (11) is then cooled to approximately 150° C., a temperature sufficiently high enough to allow combustion of the waste material, which has been partially carbonized. A limited quantity of air is introduced into the chamber allowing combustion of the waste material and the combustion products are removed from the chamber.

16 Claims, 1 Drawing Sheet

SANITARY WASTE DISPOSAL UNIT

TECHNICAL FIELD

The present invention relates to a sanitary waste disposal unit.

BACKGROUND OF THE INVENTION

The current and planned regulations regarding "Duty of Care" to the safe treatment and disposal of all blood products relates directly to their treatment and disposal at sea. Furthermore, the sanitary waste can and does block drains, particularly small diameter systems which are increasingly being fitted. It can also fail to be destroyed in septic tanks, cause difficulties in sewage treatment plants and fail to sink when disposed of at sea.

SUMMARY OF THE INVENTION

The object of the present invention is to provided a unit for disposing of sanitary waste.

According to the invention there is provided a sanitary waste disposal unit comprising:

a destruction chamber which is openable for reception of sanitary waste and closable for evacuation;

means for evacuating air from the destruction chamber;

means for heating the chamber when evacuated; and means for a controlled introduction of air into the heated evacuation chamber for combustion of sanitary waste heated in the chamber.

In use:

1. the sanitary waste is introduced to the chamber;
2. the chamber is evacuated to remove sufficient oxygen to avoid combustion;
3. the chamber and the contained waste is heated to sterilise the waste;
4. the chamber and contents is cooled to a temperature still sufficiently high for the material to combust;
5. air is introduced into the chamber to allow combustion of the material;
6. the chamber is emptied.

The destruction chamber can be emptied by flushing with water or by application of a vacuum.

The means for evacuation means may be a vacuum pump incorporated in the sanitary waste disposal unit. Alternatively the evacuation means may be a connection to a vacuum system of a ship or building in which the unit is installed.

Normally the destruction chamber will be arranged beneath a reception chamber for additional waste to be stored in if the unit is already processing waste.

For the avoidance of odours escaping from the unit, the destruction chamber may be kept at reduced pressure even when not operational. Additionally or alternatively a deodoriser may be introduced into the chamber.

BRIEF DESCRIPTION OF THE DRAWINGS

To help understanding of the invention, a specific embodiment thereof will now be described with reference to the accompanying drawing, in which.

BEST MODE FOR CARRYING OUT THE INVENTION

Figure 1:
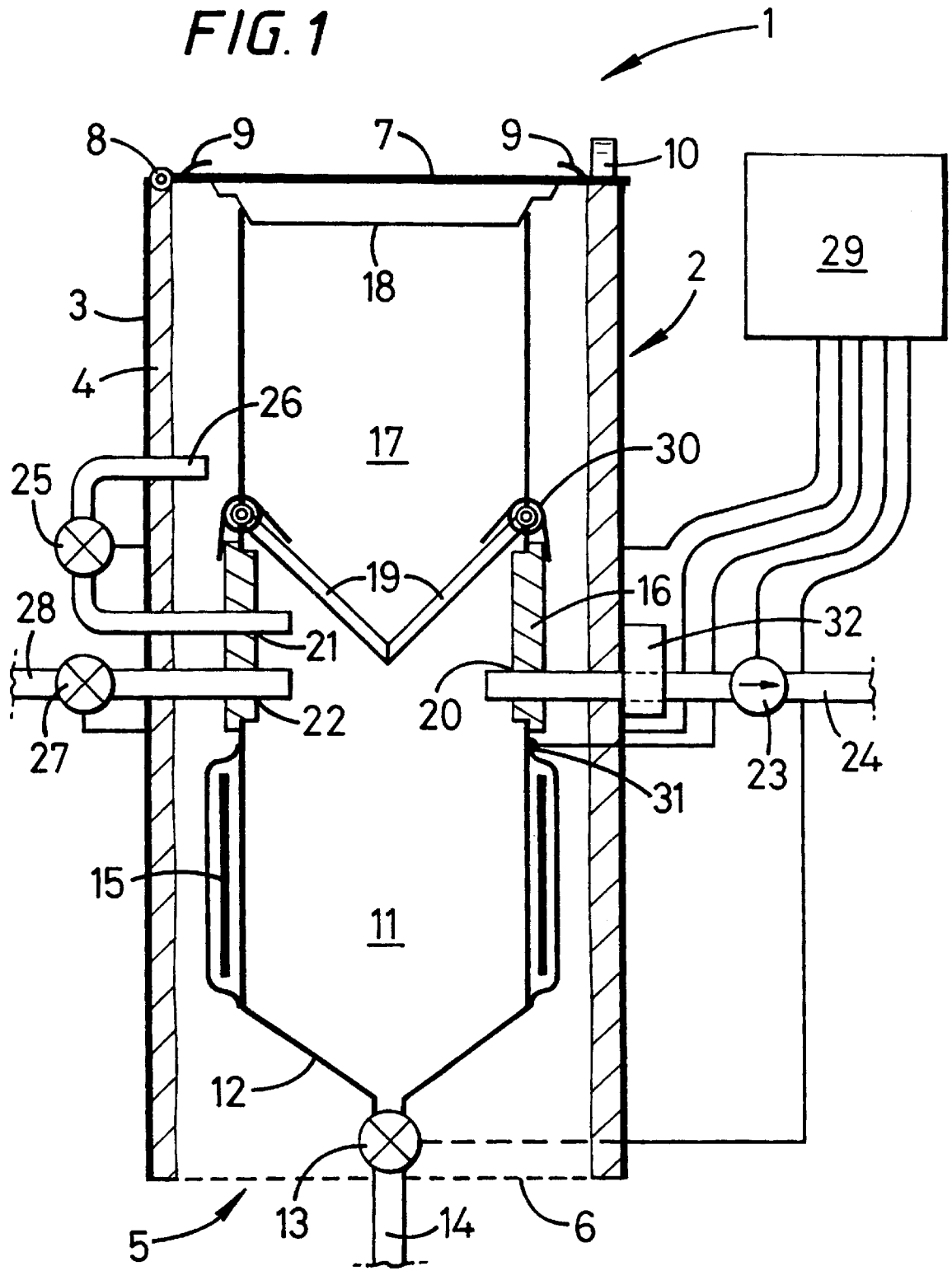
FIG. 1 is a cross-sectional side view of a sanitary waste disposal unit of the invention.

The unit 1 has a case 2 of sheet steel 3 lined with insulating material 4. The case has an open base 5 with a protective mesh 6. A lid 7 hinged at one side 8 to the case has louvres 9 and a handle 10.

Mounted within the case 2 is a vacuum chamber 11 of stainless steel. It has a tapered bottom 12 leading to a shut off valve 13. Beyond the valve, the unit is plumbed 14 to a soil pipe (not shown). The vacuum chamber has ohmic with heaters 15 attached to its side walls. At the top of the walls, an insulating ceramic ring 16 is provided and above this a similar, reception chamber 17 extends up. A closure member 18, fastened to the underside of the lid 7 closes the top of the reception chamber.

A pair of flaps 19 are hinged at the bottom of the reception chamber for opening downwards to allow waste material in the reception chamber to fall into the vacuum chamber. The ring 16 has three points 20, 21, 22. The first point 20 leads to a vacuum pump 23, whose outlet is plumbed 24 to the non-shown soil pipe. A filter 30, between the chamber 11 and the vacuum pump 23 protects the vacuum pump from any tar and other deposits produced by the waste material on heating the filter is typically a tar removing filter. This vacuum pump may be a stand alone pump, or may be a ships vacuum system. The second pipe 21 leads to an air valve 25 having an inlet 26 within the case 2. The third port 22 has a water valve 27 to which a water supply 28, typically sea water on board ship leads.

The unit is controlled by a control unit 29, which specifically controls the outlet valve 13, the heaters 15, the vacuum pump 23, the air inlet vase 25 and the water inlet valve 27.

In use the lid 7 is lifted and waste material is dropped into the reception chamber 17. On re-closure of the lid, the flaps 19 are opened by a non-shown handle. The waste material drops into the vacuum chamber 11 and the flaps 19 are closed by springs 30. A non-shown interlock prevents their opening prior to completion of the destruction cycle. The control unit is initiated.

The pump 23 is started and draws a vacuum in the vacuum chamber. The heaters 15 are switched on and the contents of the vacuum chamber, but not of the reception chamber 17 due to the insulating ring 16, are heated. The heating, typically to 300–500° C., drives off any volatile material in absense of oxygen, whereby the risk of explosive ignition is avoided. The volatiles are drawn by the pump 23 to the soil pipe. At this stage some of the waste has been at least partially converted to charcoal. After a safe period of time, the heaters are switched off after the chamber has cooled, as measured by a thermocouple 31, to 150° C., the air valve 25 is opened to admit air for combustion of the waste. The vacuum pump continues to draw gas, including the products of combustion, from the vacuum chamber and pass these to the non-shown soil pipe. The filter 30 prevents the tar and other solid residues from collecting in the soil pipe. Again after a period of time suitable for reasonably complete combustion, the waste material that is left comprises a few charred remains. The air valve and the vacuum pump are isolated and the chamber is flushed out to the soil pipe by opening of the water valve 29. Alternatively the waste may be removed from the chamber by vacuum to the soil pipe 14. After a suitable period, the entire cycle can be repeated. If necessary, further waste material can be added to the reception chamber prior to completion of the cycle. It is processed in a new cycle after completion of the previous one.

Occasionally, to clean the waste disposal unit, water is introduced into the chamber 11 and the heaters 15 are switched on. After a few minutes the heater are switched off and the chamber is emptied. In the embodiment shown, where the chamber is emptied by flushing with water, it is the flushing water which is introduced into the chamber for cleaning. Alternatively where the chamber is emptied by the application of a vacuum, the cleaning water will be loaded into the chamber through the lid 7, and emptied by the application of vacuum.

What is claimed is:

1. A method of destruction of sanitary waste comprising the steps of:

introducing waste material into a destruction chamber;

evacuating the chamber to remove sufficient oxygen to avoid combustion;

heating the chamber and the contained waste material to sterilise the waste material;

cooling the chamber and contents of the chamber to a temperature still sufficiently high for combustion of the material;

introducing air into the chamber to allow combustion of the waste material; and emptying the chamber.

2. A method as claimed in claim 1, wherein the chamber is heated to a temperature of 300–500° C.

3. A method as claimed in claim 2, wherein the chamber is cooled to a temperature of approximately 150° C. before the introduction of air.

4. A method as claimed in claim 3, wherein the chamber is emptied by flushing with water.

5. A method as claimed in claim 3, wherein the chamber is emptied by application of a vacuum to its base.

6. A method as claimed in claim 5, including the introduction of a deodoriser to the chamber.

7. A sanitary waste disposal unit comprising:

a destruction chamber which is openable for reception of sanitary waste and closable for evacuation;

means for evacuating air from the destruction chamber;

means for heating the chamber when evacuated; and means for a controlled introduction of air into the heated evacuated chamber for combustion of sanitary waste heated in the chamber, wherein the sanitary waste disposal unit is adapted and arranged to control the evacuation means to maintain the destruction chamber between ambient pressure and the pressure to which the chamber is reduced during heating even when not operational to prevent odours from escaping the chamber.

8. A sanitary waste disposal unit as claimed in claim 7, wherein the destruction chamber is arranged beneath a reception chamber for storage of additional sanitary waste while the destruction chamber is in operation.

9. A sanitary waste disposal unit as claimed in claim 8, including means for emptying combustion residue from the destruction chamber with water.

10. A sanitary waste disposal unit as claimed in claim 8, including means for emptying combustion residue from the destruction chamber by vacuum at a base of the chamber.

11. A sanitary waste disposal unit as claimed in claim 10, wherein the evacuation means is a vacuum pump incorporated in the sanitary waste disposal unit.

12. A sanitary waste disposal unit as claimed in claim 10, wherein the evacuation means is a connection to a vacuum system of a ship or building in which the unit is installed.

13. A sanitary waste disposal unit as claimed in claim 12, including a filter between the chamber and a vacuum pump to capture any tar and other combustion products.

14. A sanitary waste disposal unit as claimed in claim 13, including means for the introduction of a deodoriser into the destruction and/or reception chambers.

15. A sanitary waste disposal unit as claimed in claim 14, wherein heating means are ohmic heaters attached to side walls of the destruction chamber.

16. A sanitary waste disposal unit as claimed in claim 15, wherein the heating means is adapted to heat to a temperature of 300–500° C.

* * * * *

UNITED STATES PATENT AND TRADEMARK OFFICE
CERTIFICATE OF CORRECTION

PATENT NO. : 6,360,679 B1
DATED : March 26, 2002
INVENTOR(S) : Howard Morgan Clarke It is certified that error appears in the above-identified patent and that said Letters Patent is hereby corrected as shown below:

Column 2,
Line 15, "points" should be -- ports --.
Line 15, "point" should be -- port --.
Line 20, after "heating" delete "the" and insert -- .　The --.
Line 28, "vase" should be -- valve --.

Signed and Sealed this

Third Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,360,679 B1  
DATED : March 26, 2002  
INVENTOR(S) : Howard Morgan Clarke It is certified that error appears in the above-identified patent and that said Letters Patent is hereby corrected as shown below:

<u>Title page,</u>  
Item [56], References Cited, FOREIGN PATENT DOCUMENTS, insert the following:

-- 2310485    Aug. 27, 1997    United Kingdom  
   9508077    Not avail.    International  
   9817950    Apr 30, 1998    International --

Signed and Sealed this

Fourteenth Day of December, 2004

JON W. DUDAS  
*Director of the United States Patent and Trademark Office*